US012102548B2

(12) United States Patent
Davis et al.

(10) Patent No.: US 12,102,548 B2
(45) Date of Patent: Oct. 1, 2024

(54) LEG PROTECTOR FOR ABOVE-KNEE AMPUTATION

(71) Applicant: Osborn Medical Corporation, Centennial, CO (US)

(72) Inventors: William D. Davis, Denver, CO (US); Ian P. MacDonald, Denver, CO (US)

(73) Assignee: Osborn Medical Corporation, Centennial, CO (US)

( * ) Notice: Subject to any disclaimer, the term of this patent is extended or adjusted under 35 U.S.C. 154(b) by 89 days.

(21) Appl. No.: 17/500,592

(22) Filed: Oct. 13, 2021

(65) Prior Publication Data

US 2023/0000653 A1 Jan. 5, 2023

Related U.S. Application Data

(60) Provisional application No. 63/216,929, filed on Jun. 30, 2021.

(51) Int. Cl.
*A61F 5/01* (2006.01)

(52) U.S. Cl.
CPC ..................... *A61F 5/01* (2013.01)

(58) Field of Classification Search
CPC .. A61F 2/78; A61F 2/7812; A61F 2/80; A61F 2002/7862; A61F 2002/7868; A61F 2/64; A61F 5/01; A61F 5/0123–0127; A61F 5/0102–0109; A61F 2005/0172; A61F 13/06; A61F 13/061; A61F 13/08; A61F 13/14

USPC ...................... 128/888, 892, 894; 602/60, 62
See application file for complete search history.

(56) References Cited

U.S. PATENT DOCUMENTS

| | | | | |
|---|---|---|---|---|
| 1,858,974 A | * | 5/1932 | Swain | A61F 2/78 623/31 |
| 7,641,625 B2 | * | 1/2010 | Nobbe | A61F 2/7812 128/105.1 |
| 8,827,941 B2 | | 9/2014 | Davis | |
| 9,788,976 B1 | * | 10/2017 | Thompson | A61F 2/78 |
| 2013/0204396 A1 | * | 8/2013 | Davis | A61F 2/80 623/36 |
| 2016/0058634 A1 | * | 3/2016 | Wagner | A61F 15/006 602/12 |
| 2018/0185175 A1 | * | 7/2018 | Whiteside | A61F 2/78 |
| 2018/0344532 A1 | * | 12/2018 | Karadsheh | A61F 13/00059 |
| 2020/0170810 A1 | * | 6/2020 | Donovan | A61F 2/78 |

\* cited by examiner

*Primary Examiner* — Tarla R Patel
(74) *Attorney, Agent, or Firm* — Merchant & Gould P.C.

(57) ABSTRACT

A kit for removably dressing a leg amputated above-knee is described. The kit includes a leg protector having a thigh piece configured to wrap around a thigh of the leg, and an end piece configured to removably attach to the thigh piece, and to wrap around a distal end of the leg. A belt is configured to be secured around a torso. One or more limb attachment straps are each configured to attach the belt to at least one of the thigh piece or the end piece to anchor the leg protector to the torso.

6 Claims, 18 Drawing Sheets

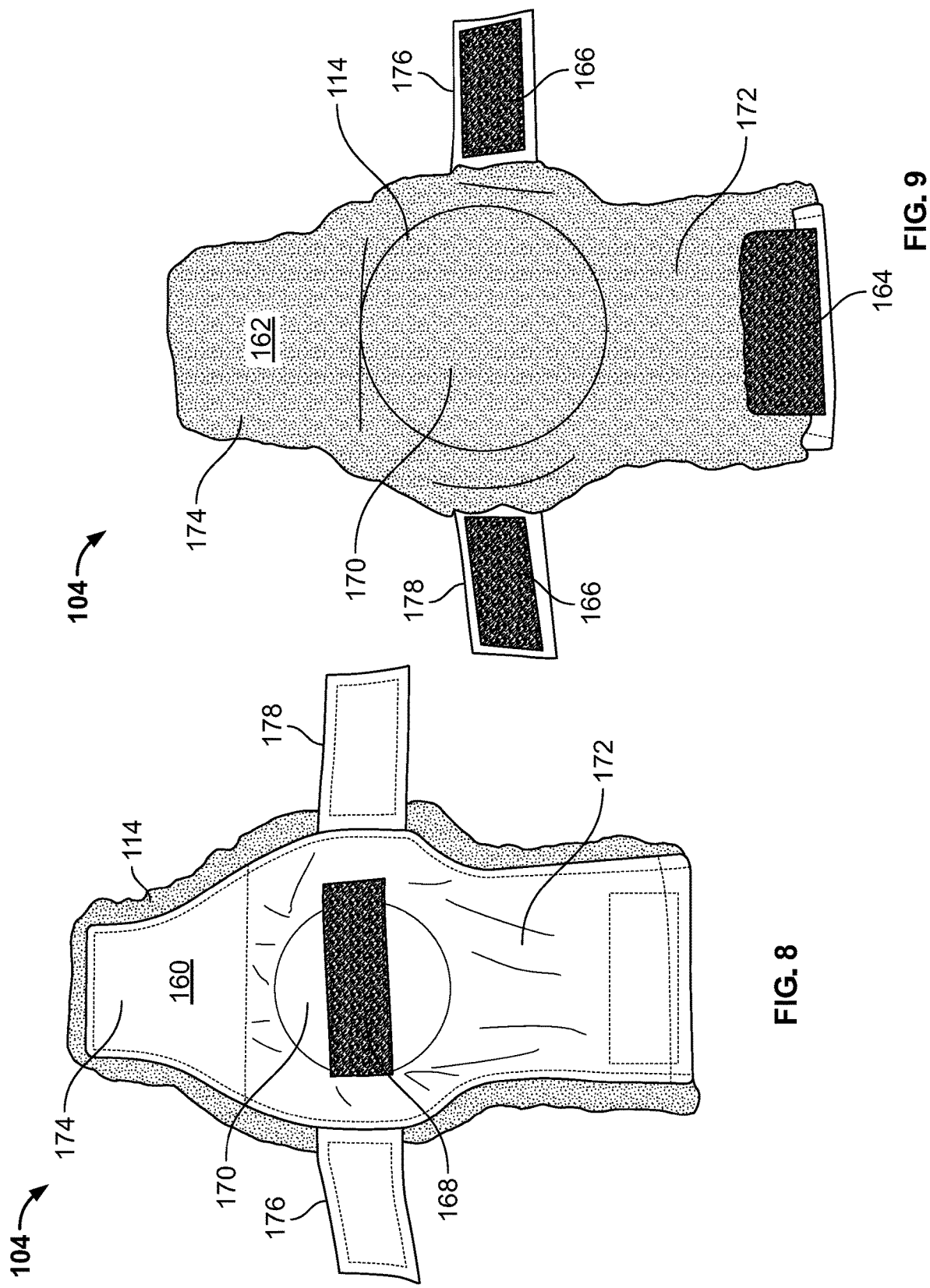

LEG PROTECTOR FOR ABOVE-KNEE AMPUTATION

CROSS-REFERENCE TO RELATED APPLICATIONS

This application claims priority to U.S. Patent Application No. 63/216,929 filed on Jun. 30, 2021, the disclosure of which is incorporated herein by reference in its entirety.

BACKGROUND

An above-knee amputation is a surgical procedure performed to remove a portion of the leg above the knee joint when the leg has been severely damaged or diseased. Conditions that may require an above-knee amputation include peripheral vascular disease, diabetes, infections, gangrene, trauma that causes the lower leg to be crushed or severed, and cancer.

Most above-knee amputations are performed due to peripheral vascular disease which causes reduce blood flow to the limbs. Poor circulation limits healing and immune responses to an injury or an infection which may spread and become life threatening. Above-knee amputations are performed when blood flow is inadequate, or when an infection is so severe that it prohibits a lower-level surgery.

During an above-knee amputation, the diseased or injured part of the leg is removed, while the healthy tissue and bone is kept as much as possible. The surgeon shapes the remaining limb to allow the best use of a prosthetic leg after recovery. After surgery, it is important to protect the wound so that it can heal properly.

SUMMARY

In general terms, the present disclosure relates to a removable dressing that is configured to protect a wound from an above-knee amputation. Various aspects are described in this disclosure, which include, but are not limited to, the following aspects.

One aspect relates to a kit for removably dressing a leg amputated above-knee. The kit comprises a leg protector, the leg protector including: a thigh piece configured to wrap around a thigh of the leg; and an end piece configured to removably attach to the thigh piece, and to wrap around a distal end of the leg; a belt configured to be secured around a torso; and one or more limb attachment straps, each limb attachment strap configured to attach the belt to at least one of the thigh piece or the end piece to anchor the leg protector to the torso.

Another aspect relates to a method of attaching a leg protector to a leg amputated above-knee. The method comprises wrapping an end piece about an axis of rotation to cover a distal end of the leg; wrapping a thigh piece about an axis of rotation to cover a thigh of the leg such that a second distal end of the thigh piece overlaps a first distal end of the thigh piece, the axis of rotation of the thigh piece being orthogonal to the axis of rotation of the end piece; and removably attaching a fastener on an interior surface of the thigh piece to one or more fasteners on an exterior surface of the thigh piece to secure the thigh piece and the end piece around the leg amputated above-knee.

Another aspect relates to a leg protector for a leg amputated above-knee. The leg protector comprises a thigh piece configured to wrap around a first axis of rotation to wrap around a thigh of the leg amputated above-knee; and an end piece configured to removably attach to the thigh piece, and to wrap around a second axis of rotation to wrap around a distal end of the leg amputated above-knee, wherein the second axis of rotation is orthogonal to the first axis of rotation.

BRIEF DESCRIPTION OF THE DRAWINGS

The following drawing figures, which form a part of this application, are illustrative of the described technology and are not meant to limit the scope of the disclosure in any manner.

FIG. 8 is a plan view of an exterior surface of an end piece of the leg protector of FIG. 1, the end piece shown detached from the thigh piece.

FIG. 9 is a plan view of an interior surface of the end piece of FIG. 8, the end piece shown detached from the thigh piece.

DETAILED DESCRIPTION

Figure 1:
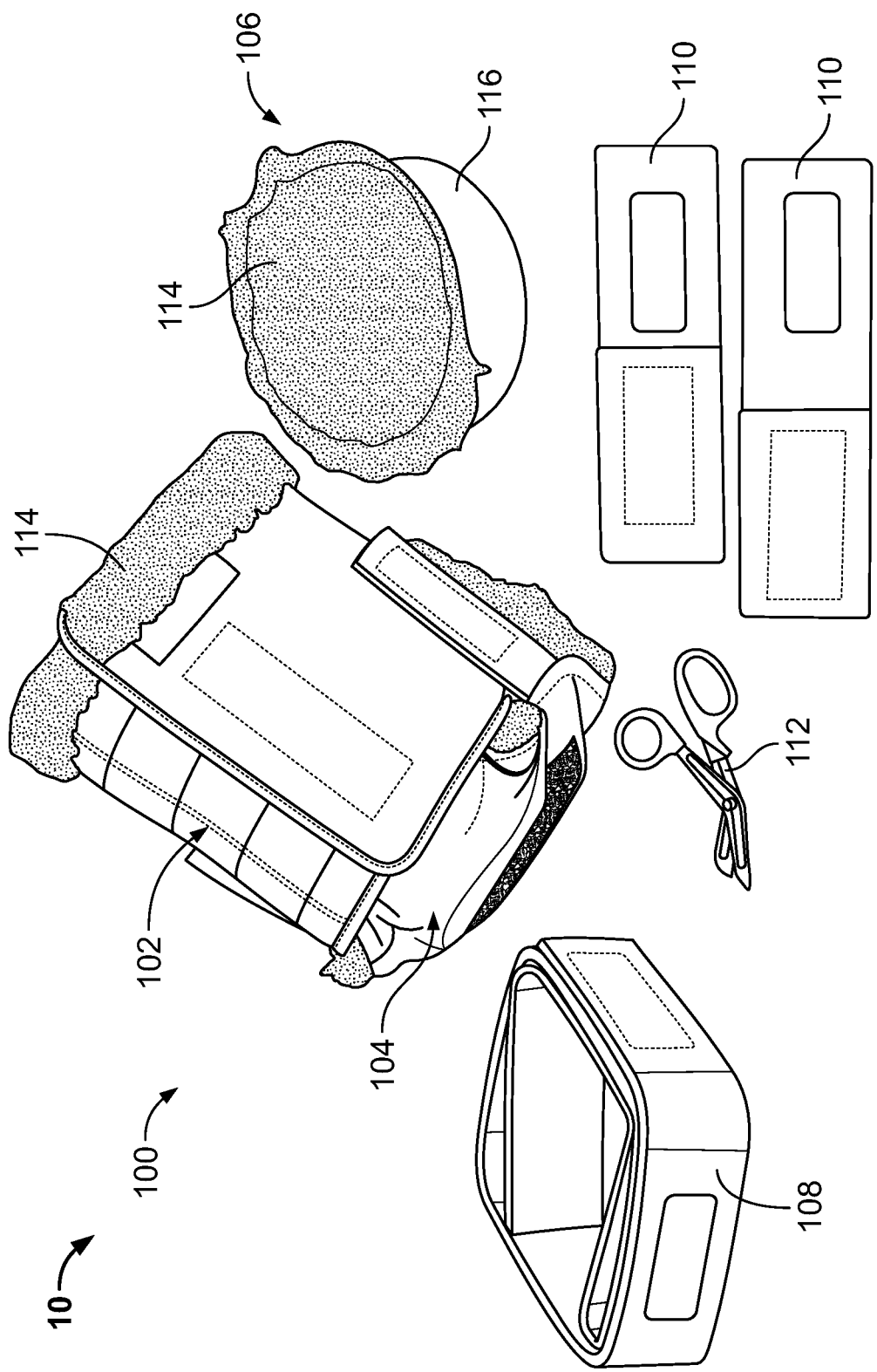
FIG. 1 is a view of a kit that includes a leg protector in accordance with certain examples of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 shows a kit 10 that includes a leg protector 100. The leg protector 100 is a removable dressing that protects a wound from dehiscence after an above-knee amputation. The leg protector 100 is therapeutic and promotes healing by providing warmth and cushioning for the amputated leg. The leg protector 100 includes a number of separate pieces that attach to each other. When assembled, the leg protector 100 covers, warms, and protects the amputated leg.

The leg protector 100 includes a thigh piece 102 that is configured to wrap around the thigh of the amputated leg. The leg protector 100 further includes an end piece 104 that is configured to removably attach to the thigh piece 102, and to wrap around a distal end (i.e., stump) of the amputated leg. The thigh piece 102 and the end piece 104 are shown in FIGS. 2-11, and will be described in more detail below.

The leg protector 100 can include a distal spacer 106 that is configured to reduce or eliminate a space between an interior surface of the end piece 104 and the distal end of the amputated leg to provide additional cushioning and protection. For example, the distal spacer 106 can include a body portion 116 that is lined with a padding material 114 for cushioning and warming the stump of the amputated leg. The body portion 116 can include a foam layer that is at least partially surrounded by an outer layer of an air-permeable and durable fabric material.

The interior surfaces of the thigh piece 102 and the end piece 104 can also be lined with the padding material 114. The padding material is washable such that the leg protector 100 is configured for extended wear and use. The padding material 114 is made from a light and soft or airy material such as fleece, wool, cotton, or similar types of materials.

The thigh piece 102, end piece 104, and distal spacer 106 can protect a leg amputated above-knee from impact with an object whether from a patient fall, an object falling onto the amputated leg, or from accidentally banging the amputated leg into another object. For example, the thigh piece 102, end piece 104, and distal spacer 106 can each include foam layers as well as the padding material 114 to cushion and protect the amputated leg from impacts with objects. The cushioning and protection provided by the leg protector 100 may help to prevent dehiscence of the wound, which can cause severe pain, bleeding, and inflammation.

Additionally, the thigh piece 102, end piece 104, and distal spacer 106 warm the amputated leg with minimal skin trauma (e.g. ulcerations, cracking, and/or abrasions). For example, the padding material 114 allows the thigh piece 102 end piece 104, and distal spacer 106 to warm the amputated leg to promote vasodilatation and maintain blood circulation, while preventing ulceration or other physical degradation of the stump of the amputated leg.

The leg protector 100 is machine washable for extended use and reusability. Also, the leg protector 100 does not use any latex materials such that it is a latex-free product.

As further shown in FIG. 1, the leg protector 100 includes a belt 108 and one or more limb attachment straps 110. As will be described in more detail, the belt 108 and the one or more limb attachment straps 110 can be used to anchor the leg protector 100 to a patient's body after the leg protector is attached to a leg amputated above-knee.

Additionally, as shown in FIG. 1, the kit 10 can include scissors 112. As will be described in more detail, the scissors 112 can be used by a caregiver to trim and thereby adjust the size of the thigh piece 102 to more comfortably fit around the thigh of a patient.

Figure 2:
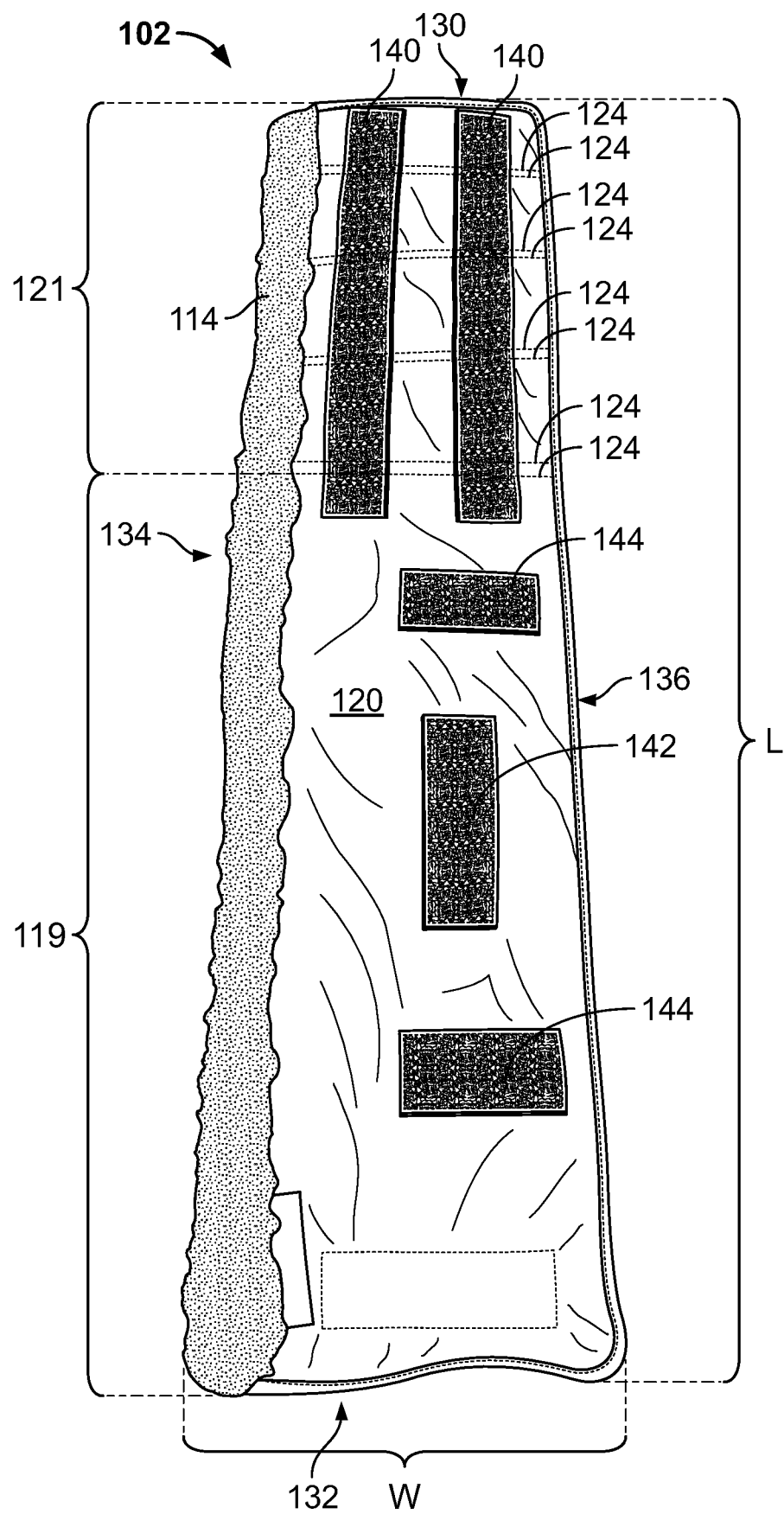
FIG. 2 is a plan view of an exterior surface of a thigh piece of the leg protector of FIG. 1, the thigh piece shown in an unwrapped condition.
Figure 3:
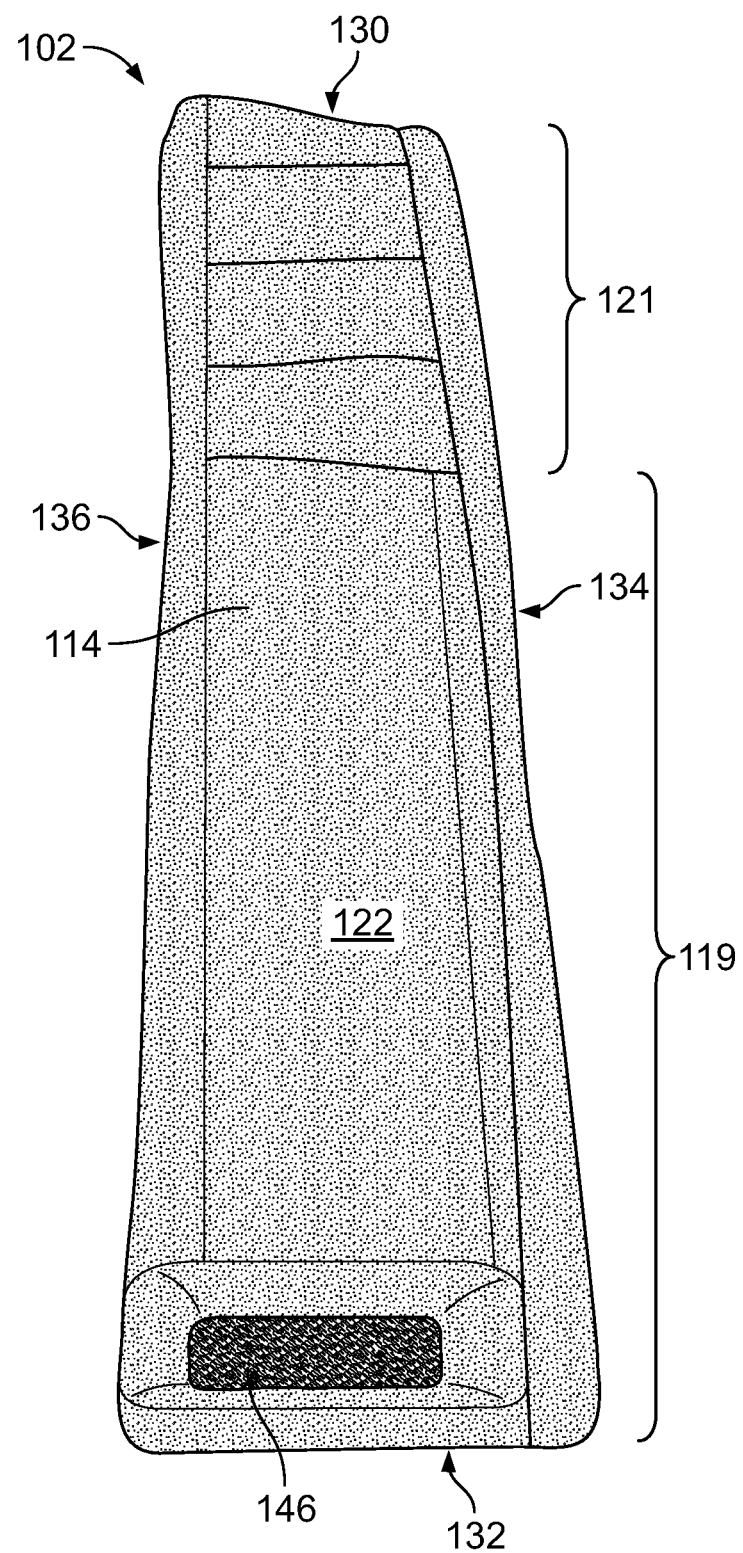
FIG. 3 is a plan view of an interior surface of the thigh piece of FIG. 2, the thigh piece shown in an unwrapped condition.

FIG. 2 is a view of an exterior surface 120 of the thigh piece 102 shown in an unwrapped condition. FIG. 3 is a view of an interior surface 122 of the thigh piece 102 shown in an unwrapped condition. Referring now to FIGS. 2 and 3, the thigh piece 102 has a first distal end 130, a second distal end 132, a first lateral side 134, and a second lateral side 136. When the leg protector 100 is worn, the first lateral side 134 is adjacent to the crotch region of the patient, and the second lateral side 136 is adjacent to the stump of the amputated leg.

The thigh piece 102 has a length L and a width W. The length L is substantially longer than the width W such that the thigh piece 102 has a substantially rectangular shape. In some examples, the length L ranges from about 40 inches to about 44 inches. In some examples, the length L is about 42 inches. In some examples, the width W ranges from about 8 inches to about 12 inches. In some examples, the width W is about 10 inches.

As shown in FIG. 2, the thigh piece 102 includes a first portion 119 and a second portion 121. As will be described in more detail below, the first portion 119 is configured to be placed at least partially under the thigh of the amputated leg and the second portion 121 is configured to be at least partially wrapped over the amputated leg.

On both the first and second portions 119, 121, the exterior surface 120 is made from a fabric material that is air-permeable and durable. On both the first and second portions 119, 121, the interior surface 122 is lined with the padding material 114.

As shown in FIG. 2, the padding material 114 extends over the first lateral side 134. Advantageously, this can provide a soft boundary and cushioning adjacent to the crotch region of a patient when the leg protector 100 is worn by the patient.

Figure 4:
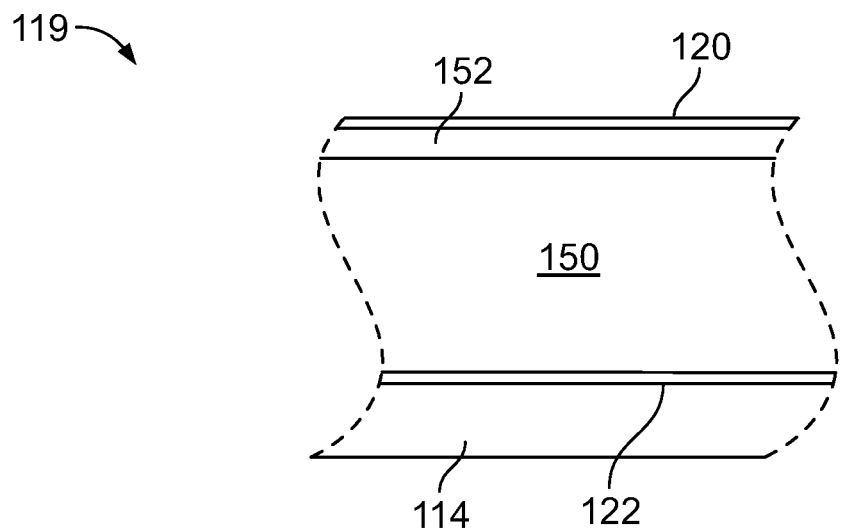
FIG. 4 is a cross-sectional view of a first portion of the thigh piece of FIG. 2.
Figure 5:
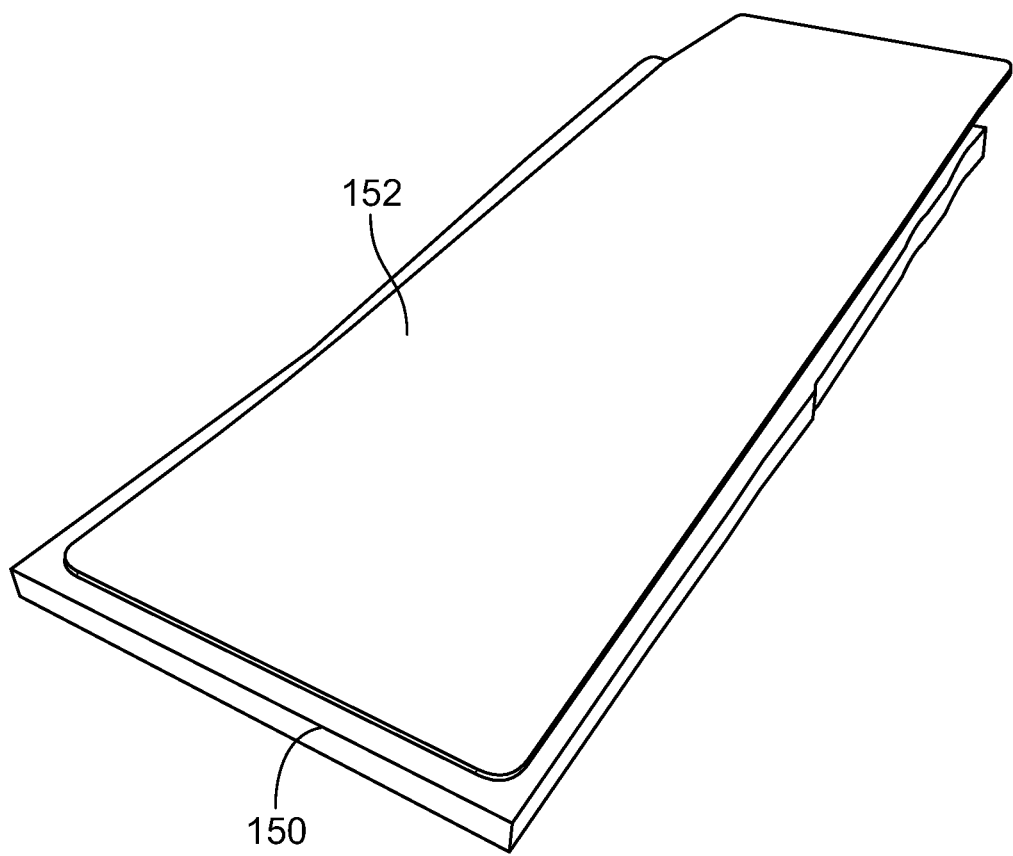
FIG. 5 is a view of a cushioning layer and a resilient layer removed from the first portion of the thigh piece.

FIG. 4 is a cross-sectional view of the first portion 119 of the thigh piece 102. FIG. 5 is a view of a cushion layer 150 and a resilient layer 152 removed from the first portion 119. Referring now to FIGS. 2-5, the first portion 119 includes the cushion layer 150 between the exterior and interior surfaces 120, 122. In some examples, the cushion layer 150 is a sheet of foam material. In some examples, the foam layer is made of closed cell urethane foam.

In some examples, the cushion layer 150 can have a length of about 17 inches to about 21 inches. In some examples, the cushion layer 150 has a length of about 19 inches. In some examples, the cushion layer 150 can have a width of about 5 inches to about 10 inches. In some examples, the cushion layer 150 has a width of about 7.5 inches.

Additionally, the first portion 119 includes the resilient layer 152 between the cushion layer 150 and the exterior surface 120. The resilient layer 152 is a sheet of flexible plastic. Advantageously, the resilient layer 152 provides rigidity to the thigh piece 102.

In some examples, the resilient layer 152 can have a length of about 20 inches to about 26 inches. In some examples, the resilient layer 152 has a length of about 23 inches. In some examples, the resilient layer 152 can have a width of about 5 inches to about 9 inches. In some examples, the resilient layer 152 has a width of about 7 inches.

Figure 6:
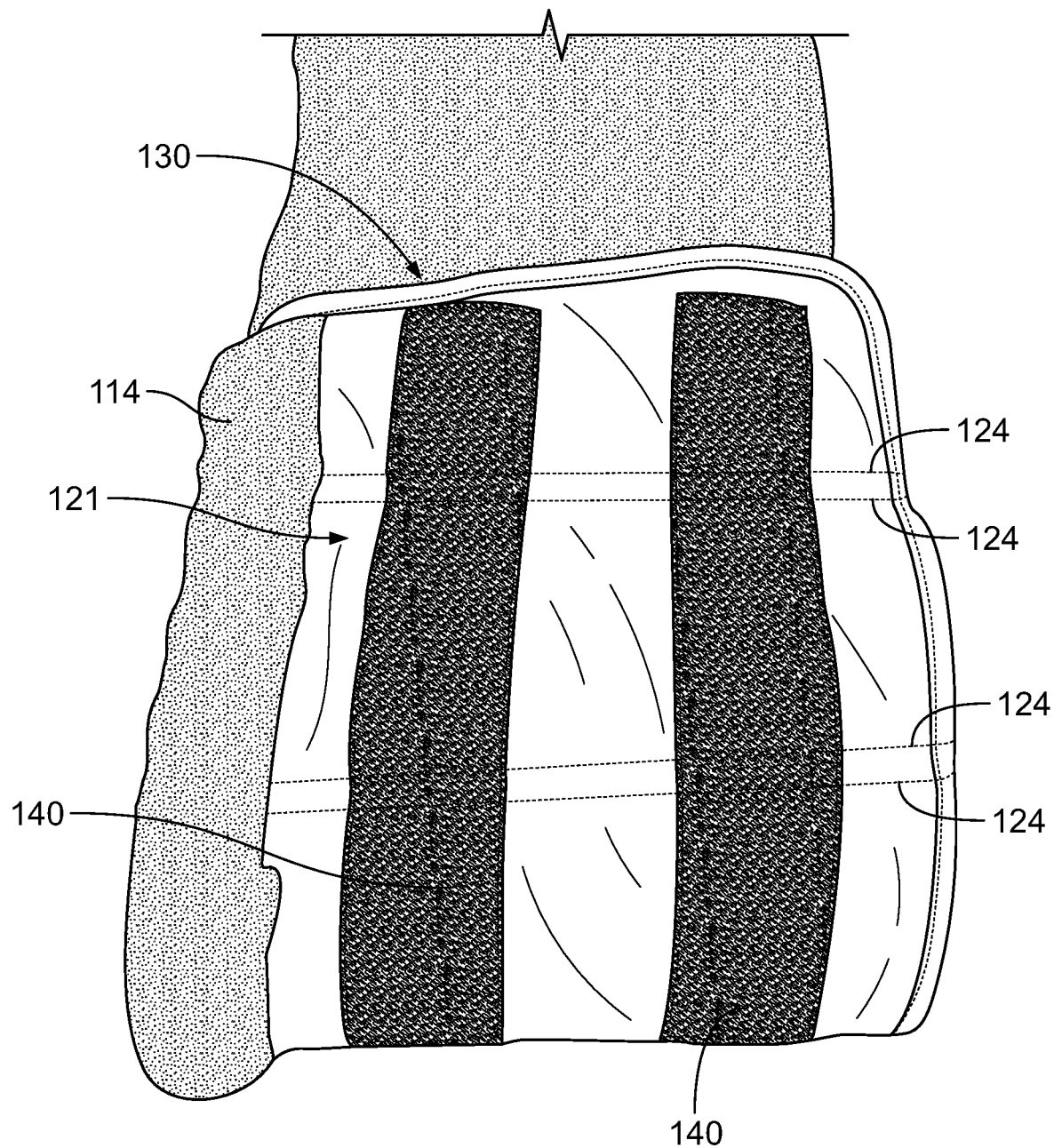
FIG. 6 is a detailed view of a second portion of the thigh piece of FIG. 2.
Figure 7:
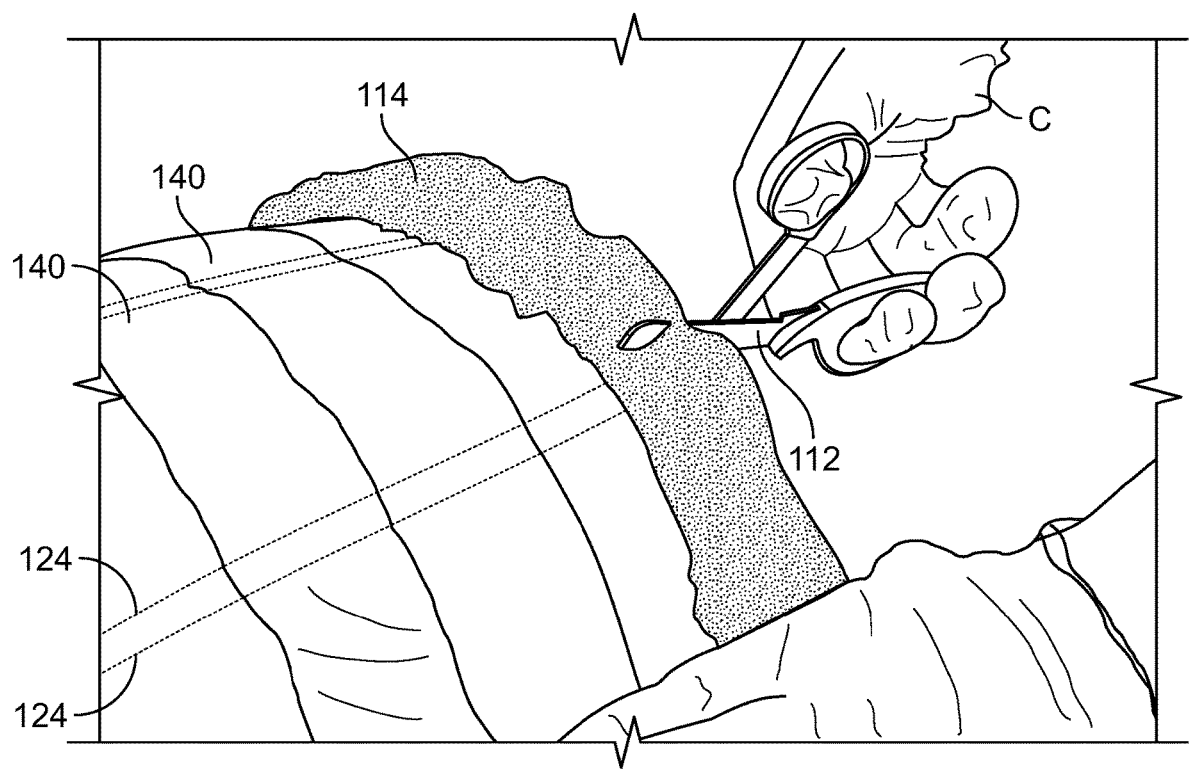
FIG. 7 is a view showing a caregiver trimming the second portion of the thigh piece using scissors from the kit of FIG. 1.

FIG. 6 is a detailed view of the second portion 121 of the thigh piece 102. FIG. 7 is a view showing a caregiver C trimming the second portion 121 using the scissors 112 of the kit 10. Referring now to FIGS. 1, 2, 6, and 7, the second portion 121 includes lines of stitching 124. While the thigh piece 102 is sized to fit most limb lengths and limb girths (e.g., one size fits most), the caregiver C can use the scissors 112 to cut between the lines of stitching 124 to reduce the length L of the thigh piece 102 while maintaining the integrity of the thigh piece 102. For example, the caregiver C can cut between the lines of stitching 124 without opening an interior volume of thigh piece 102 and causing internal materials to escape therefrom.

As shown in FIGS. 2, 6, and 7, the exterior surface 120 of the second portion 121 of the thigh piece 102 includes fasteners 140. In some examples, the fasteners 140 are hook-and-loop fasteners, hook-and-pile fasteners, or touch fasteners. In some examples, the fasteners 140 are loop fasteners. Alternatively, the fasteners 140 can be hook fasteners. Additional types of fastening mechanisms for the fasteners 140 may also be used.

As shown in FIG. 3, the interior surface 122 includes a fastener 146 that can removably attach to one or more of the fasteners 140 on the exterior surface 120. The fastener 146 can be a hook-and-loop fastener, hook-and-pile fastener, or touch fastener. In some examples, the fastener 146 is a hook fastener. Alternatively, the fastener 146 can be a loop fastener. Additional types of fastening mechanisms for the fastener 146 may also be used.

As shown in FIGS. 2 and 3, the fasteners 140 are parallel strips of material on the exterior surface 120 that extend parallel to the length L of the thigh piece 102. The fastener 146 is a strip of material on the interior surface 122 that extends parallel to the width W of the thigh piece 102. Thus, the fastener 146 is orthogonally orientated relative to the fasteners 140.

The fastener 146 can removably attach along the parallel strips of the fasteners 140 to wrap the thigh piece 102 around the thigh of an amputated leg. For example, the fastener 146 can removably attach to the parallel strips of the fasteners 140 closer toward the first distal end 130 to increase a diameter of the thigh piece 102 or loosen the thigh piece 102 around the thigh of the leg amputated above-knee. Alternatively, the fastener 146 can removably attach to the fasteners 140 closer toward the second distal end 132 to decrease the diameter of the thigh piece 102 or tighten the thigh piece 102 around the thigh of the leg amputated above-knee.

As described above, the length L of the thigh piece 102 can be reduced by cutting between the lines of stitching 124. Thus, the length L of the thigh piece 102 can be adjusted by the caregiver C when it is desirable to removably attach the fastener 146 to the fasteners 140 closer toward the second distal end 132 to accommodate thinner thigh sizes.

While the figures show the exterior surface 120 as including two parallel strips of the fasteners 140, in alternative examples, the exterior surface 120 can include a single strip of the fastener 140. Also, in some examples, the exterior surface 120 can include more than two parallel strips of the fasteners 140 such as three parallel strips of the fasteners 140, or more than three parallel strips. Additional configurations for fasteners 140 are contemplated.

Referring now to FIG. 2, the exterior surface 120 of the thigh piece 102 further includes fasteners 142, 144. The fasteners 142, 144 can be a hook-and-loop fastener, hook-and-pile fastener, or touch fastener. In some examples, the fasteners 142, 144 are loop fasteners. Alternatively, the fasteners 142, 144 can be hook fasteners. As will be described in more detail, the fasteners 142, 144 allow the end piece 104 to removably attach to the thigh piece 102.

FIGS. 8 and 9 show exterior and interior surfaces 160, 162, respectively, of the end piece 104. As shown in FIGS. 8 and 9, the end piece 104 includes a central portion 170, first and second extensions 172, 174, and first and second flaps 176, 178. The first and second extensions 172, 174 are configured to flip, fold, or pivot with respect to the central portion 170.

As shown in FIG. 8, the exterior surface 160 of the end piece 104 can be made from the same material as the exterior surface 120 of the thigh piece 102. For example, the exterior surface 160 can be made of a fabric material that is air-permeable and durable.

As shown in FIG. 9, the interior surface 162 of the end piece 104 can be made from the same material as the interior surface 122 of the thigh piece 102. For example, the interior surface 162 can be lined with the padding material 114.

The central portion 170 has a cushion layer between the exterior and interior surfaces 160, 162. The cushion layer is similar to the cushion layer 150 of the thigh piece 102. For example, the cushion layer inside the central portion 170 can be a foam layer made from a closed cell urethane foam material. In certain examples, the cushion layer inside the central portion 170 of the end piece 104 is thicker than the cushion layer 150 of the thigh piece 102 to provide additional cushioning and protection for the stump of a leg amputated above-knee.

As shown in FIG. 8, the central portion 170 can include a fastener 168. In some examples, the fastener 168 is a hook-and-loop fastener, hook-and-pile fastener, or touch fastener. In some examples, the fastener 168 is a loop fastener. Alternatively, the fastener 168 can be a hook fastener. The fastener 168 can be used as an additional location or an alternative location for attaching the one or more limb attachment straps 110 to the leg protector 100.

As shown in FIG. 9, the first extension 172 includes a fastener 164, and each of the first and second flaps 176, 178 includes a fastener 166. In some examples, the fasteners 164, 166 are hook-and-loop fasteners, hook-and-pile fasteners, or touch fasteners. In some examples, the fasteners 164, 166 are hook fasteners. Alternatively, the fasteners 164, 166 are loop fasteners.

Figure 10:
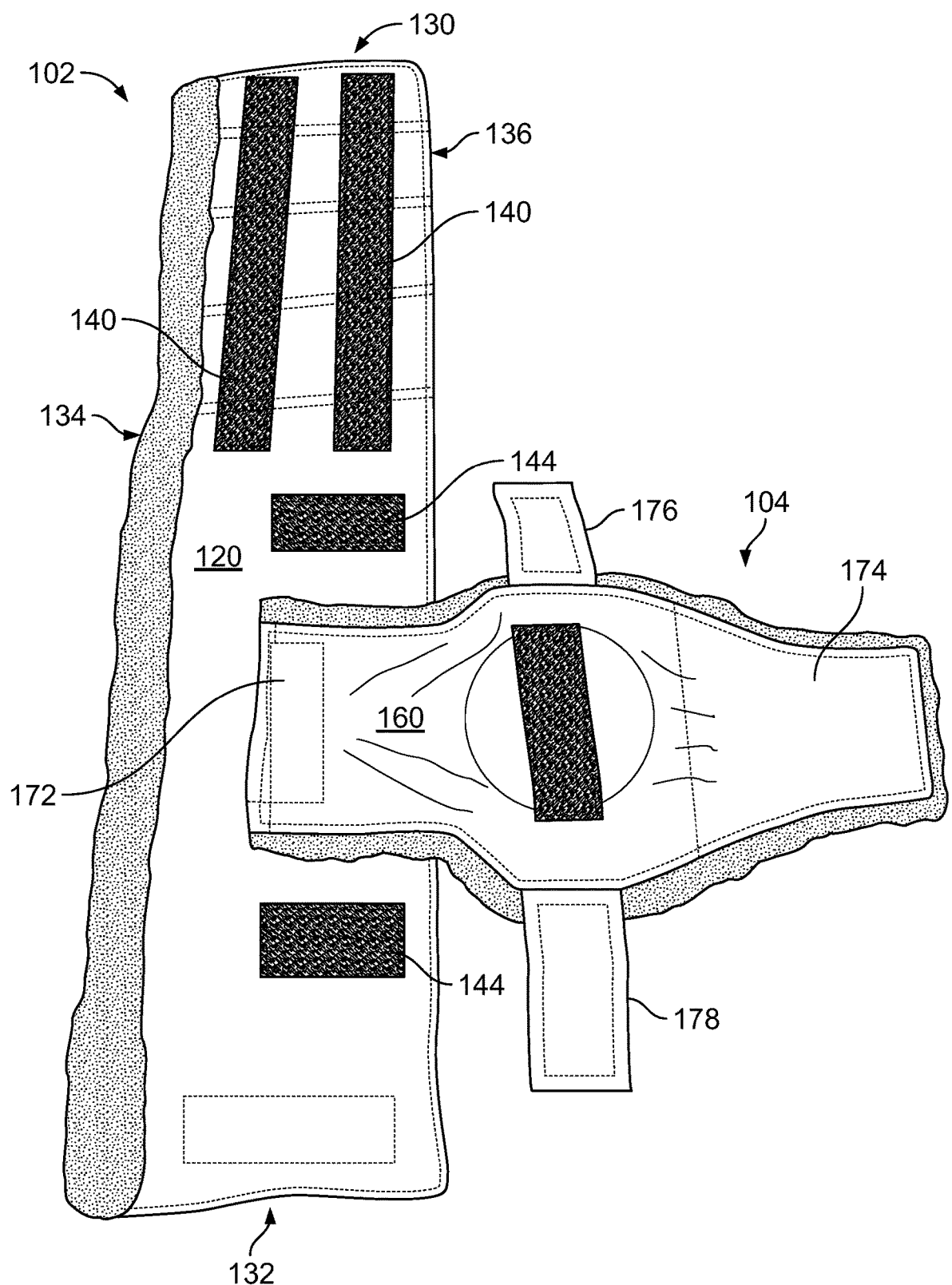
FIG. 10 is a plan view of the end piece attached to the thigh piece, the exterior surfaces of the thigh piece and the end piece are shown.
Figure 11:
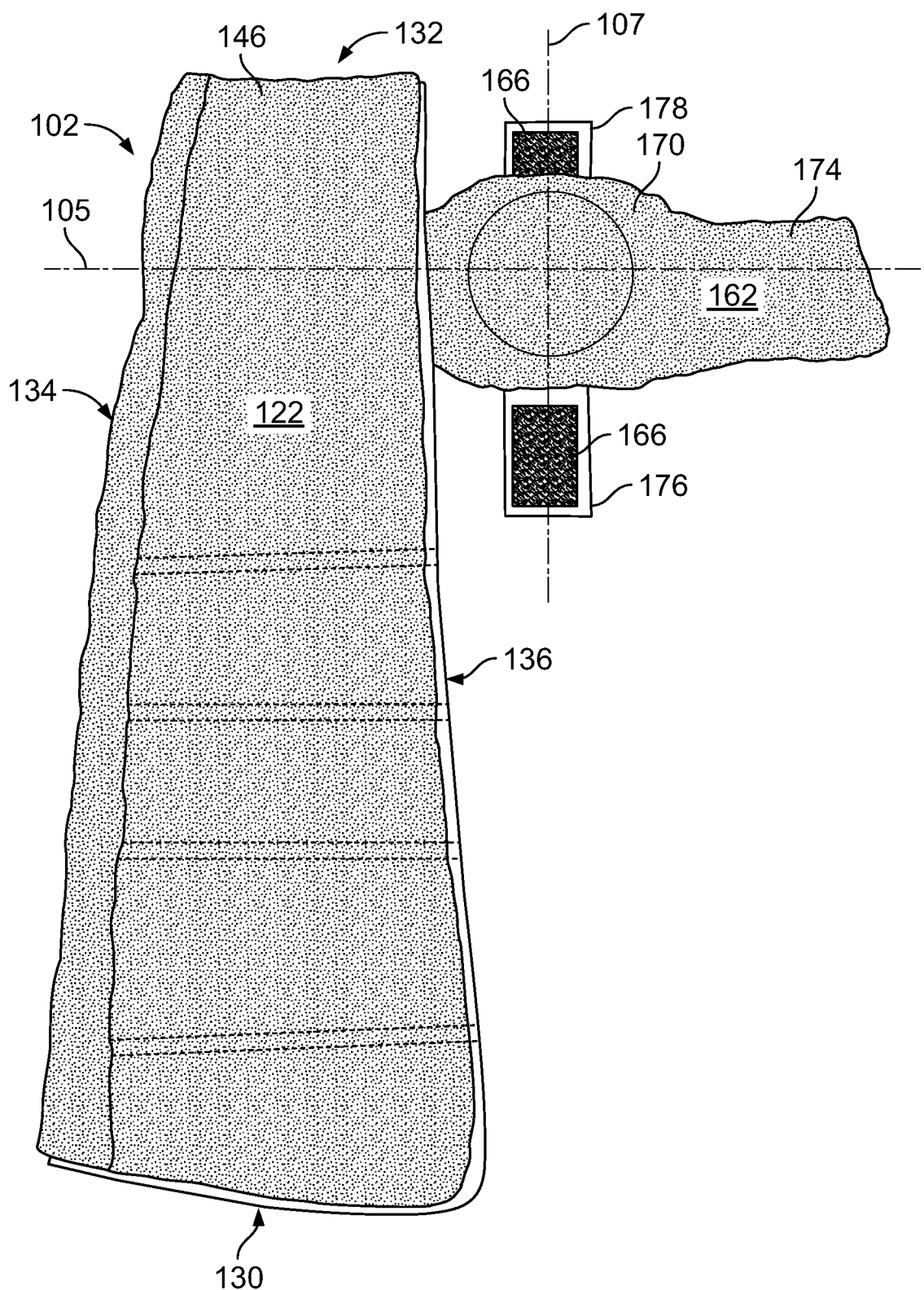
FIG. 11 is a plan view of the end piece attached to the thigh piece, the interior surfaces of the thigh piece and the end piece are shown.

FIG. 10 shows the end piece 104 attached to the thigh piece 102, with the exterior surfaces 120, 160 of the thigh piece 102 and the end piece 104 being shown. FIG. 11 shows the end piece attached to the thigh piece, the interior surfaces 122, 162 of the thigh piece 102 and the end piece 104 being shown. Referring now to FIGS. 2, 3, and 8-11, the fastener 164 on the first extension 172 of the end piece 104 can removably attach to the fastener 142 on the exterior surface 120 of the thigh piece 102 to removably attach the end piece 104 to the thigh piece 102.

Figure 12:
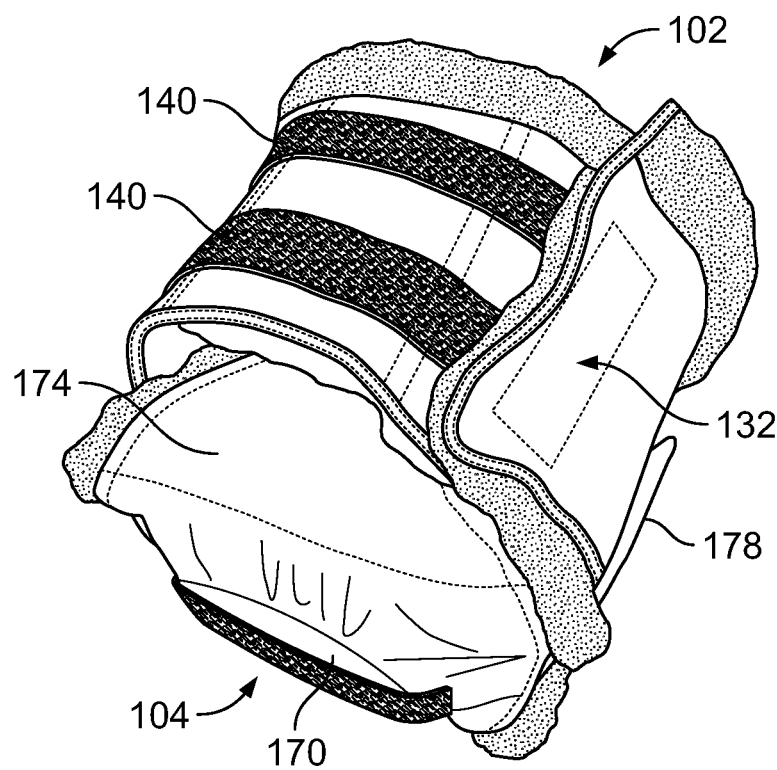
FIG. 12 is an isometric view of the end piece attached to the thigh piece, the thigh piece shown in a wrapped condition from a caregiver perspective.
Figure 13:
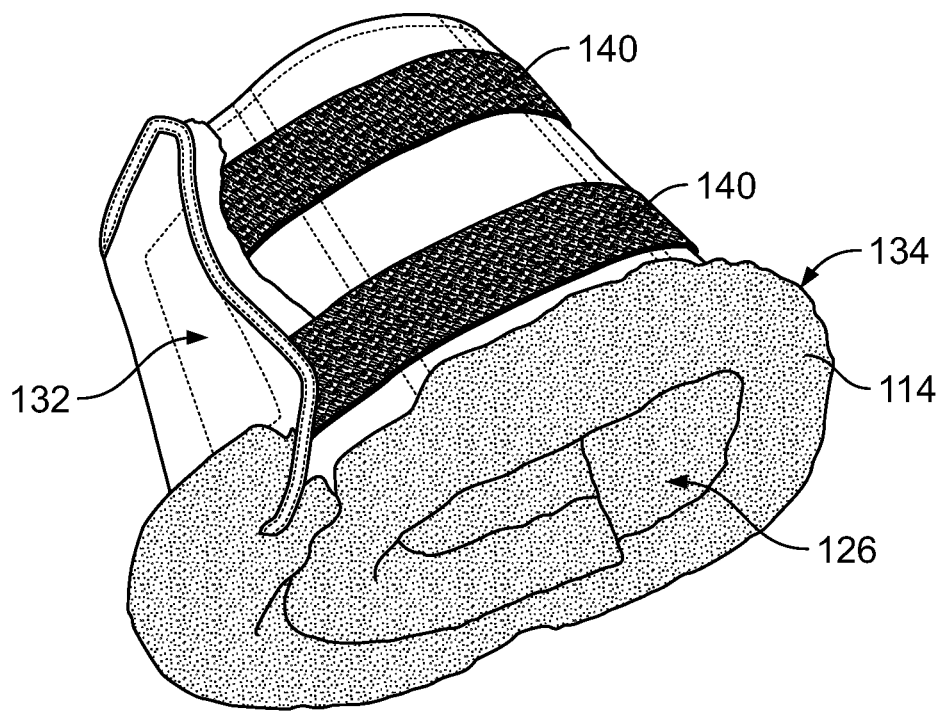
FIG. 13 is another isometric view of the end piece attached to the thigh piece, the thigh piece shown in a wrapped condition from a patient perspective.

FIG. 12 shows the end piece 104 attached to the thigh piece 102, with the thigh piece 102 shown in a wrapped condition from a caregiver perspective. FIG. 13 is another view of the end piece 104 attached to the thigh piece 102, with the thigh piece 102 shown in a wrapped condition from a patient perspective. As shown in FIG. 10, the thigh piece 102 wraps around a first axis of rotation 105 to wrap around the thigh of the amputated leg, and the end piece 104 wraps around a second axis of rotation 107 to wrap around a distal end (i.e., stump) of the amputated leg. The first and second axes of rotation 105, 107 are orthogonal to one another.

Figure 14:
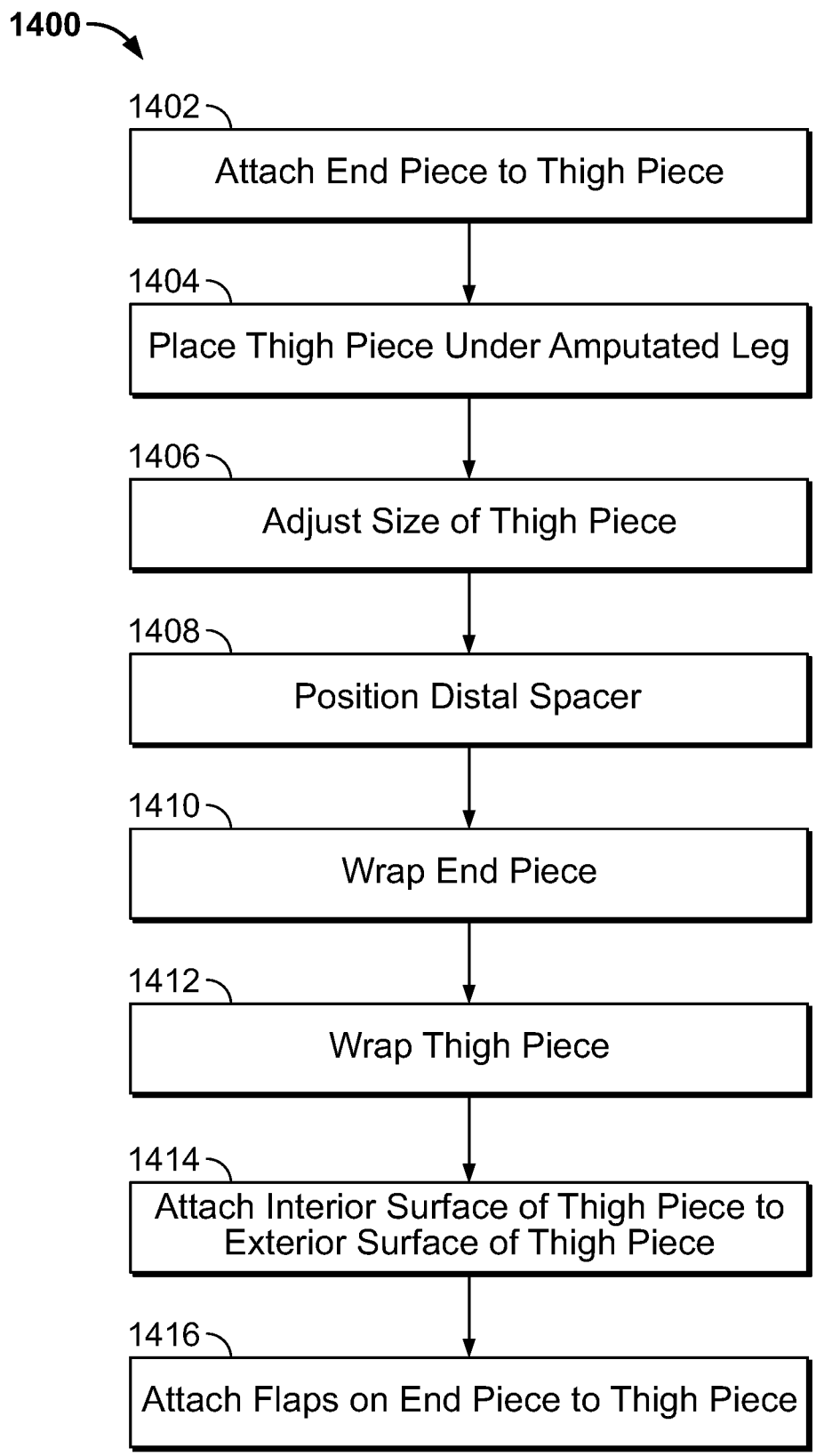
FIG. 14 illustrates a method of attaching the leg protector of FIG. 1 to a leg amputated above-knee.

FIG. 14 illustrates a method 1400 of attaching the leg protector 100 to a leg amputated above-knee. The method 1400 will now be described with reference to FIGS. 1-13, and in accordance with the above description.

Referring now to FIG. 14, the method 1400 includes an operation 1402 of removably attaching the end piece 104 to the thigh piece 102. Operation 1402 is performed by removably attaching the fastener 164 on the first extension 172 of the end piece 104 (see FIG. 9) to the fastener 142 on the exterior surface 120 of the thigh piece 102 (see FIG. 2) to removably attach the end piece 104 to the thigh piece 102. After completion of operation 1402, the thigh piece 102 and the end piece 104 looks like the arrangement shown in FIGS. 10 and 11, as described above.

Next, the method 1400 includes an operation 1404 of placing the thigh piece 102 under the amputated leg. Operation 1404 is performed such that the thigh piece 102 is positioned with the interior surface 122 facing upwards (see FIG. 11) such that the interior surface 122 contacts the underside of the thigh of the amputated leg. The central portion 170 of the end piece 104 should also be positioned adjacent to the distal end (i.e., stump) of the amputated leg.

The method 1400 can include an operation 1406 of adjusting the size of the thigh piece 102 by using the scissors 112 to cut between the lines of stitching 124 to reduce the length L of the thigh piece 102 such that the thigh piece 102 can fit around the thigh of the amputated leg. Operation 1406 is optional such that it in some examples it is not performed.

The method 1400 can also include an operation 1408 of positioning the distal spacer 106 on top of the central portion 170 of the end piece 104. Operation 1408 can be performed when thigh of the leg amputated above-knee is substantially shorter than the width W of the thigh piece 102. Operation 1408 is optional such that it in some examples it is not performed.

Next, the method 1400 includes an operation 1410 of wrapping the end piece 104 about the second axis of rotation 107 (see FIG. 10) to cover a distal end of the amputated leg. For example, operation 1410 can include flipping the second extension 174 towards the first lateral side 134 of the thigh piece 102 such that the central portion 170 is orthogonal to the first extension 172 which remains under the thigh of the amputated leg.

After operation 1410, the central portion 170 covers the distal end of the amputated leg. In examples where the method 1400 includes operation 1408, the distal spacer 106 abuts the distal end of the amputated leg. In examples where the method 1400 does not include operation 1408, the interior surface 162 of the end piece 104 abuts the distal end of the amputated leg.

Next, the method 1400 includes an operation 1412 of wrapping the thigh piece 102 about the first axis of rotation 105 (see FIG. 10) to wrap the thigh piece 102 around the amputated leg such that the second distal end 132 overlaps the first distal end 130, and the second extension 174 of the end piece 104 is tucked inside the thigh piece 102.

Next, the method 1400 includes an operation 1414 of removably attaching the fastener 146 on the interior surface 122 of the thigh piece 102 to one or more of the fasteners 140 on the exterior surface 120 of the thigh piece 102. This can secures the thigh piece 102 in the wrapped condition with the second extension 174 tucked inside the thigh piece 102.

Next, the method 1400 includes an operation 1416 of removably attaching the fasteners 166 on the first and second flaps 176, 178 of the end piece 104 to the fasteners 144 on the exterior surface 120 of the thigh piece 102.

After completion of operation 1416, the leg protector 100 looks like the arrangement shown in FIGS. 12 and 13. Thus, the thigh piece 102 covers and protects the thigh of the leg amputated above-knee, while the end piece 104 covers and protects the distal end of the leg.

As shown in FIG. 13, the thigh piece 102 and the end piece 104 together define a cavity 126 which is configured to be occupied by the amputated leg when the leg protector 100 is worn by a patient. As further shown in FIG. 13, the padding material 114 extends over the first lateral side 134 such that it provides a soft boundary and cushioning adjacent to the crotch region of a patient when the leg protector 100 is worn by the patient.

Figure 15:
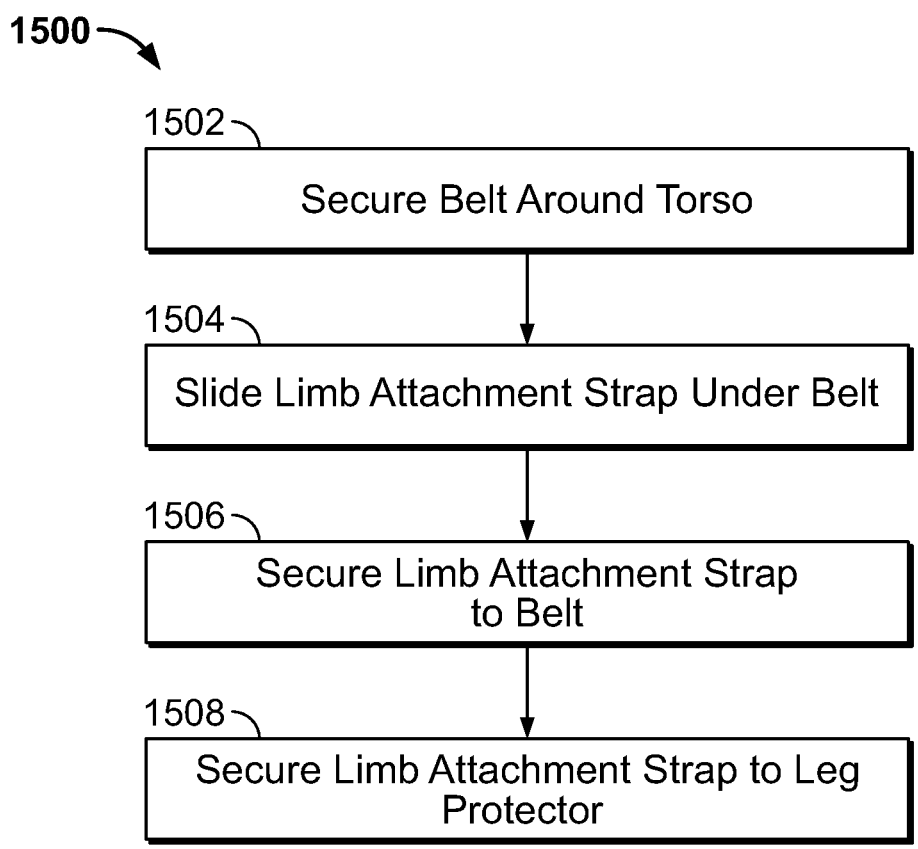
FIG. 15 illustrates a method of anchoring the leg protector to a patient's body after the leg protector is attached to the leg amputated above-knee.

FIG. 15 illustrates a method 1500 of anchoring the leg protector 100 to a patient's body after the leg protector 100 is attached to the leg amputated above-knee. Accordingly, the method 1500 can be performed after completion of the method 1400.

Figure 16:
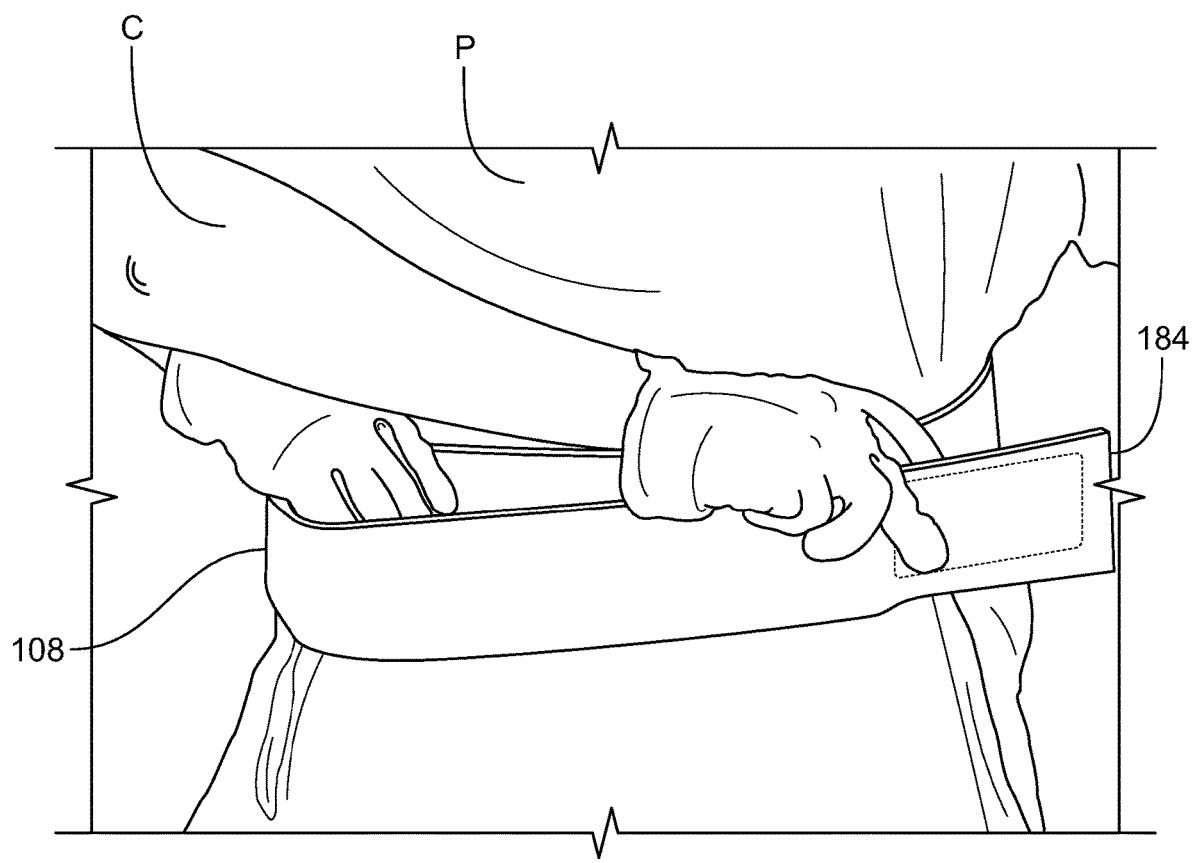
FIG. 16 shows an operation of the method of FIG. 15 being performed by a caregiver to secure a belt of the kit of FIG. 1 around a torso of a patient.

The method 1500 includes an operation 1502 of securing the belt 108 of the kit 10 (shown in FIG. 1) around a patient's torso. FIG. 16 shows operation 1502 being performed by a caregiver C to secure the belt 108 around a torso of a patient P. As shown in FIG. 16, the belt 108 is wrapped around the waist of the patient P. Alternatively, such as when the patient P is obese, the belt 108 can be wrapped above the gut or around the chest of the patient P.

Figure 17:
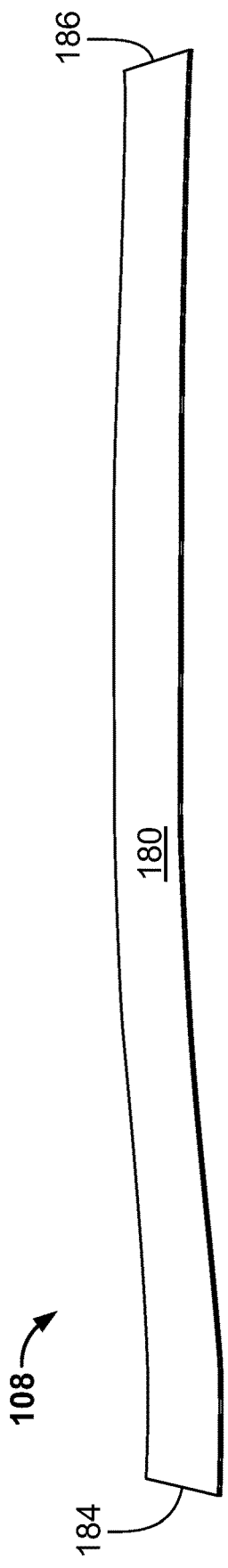
FIG. 17 shows a first side of the belt.
Figure 18:
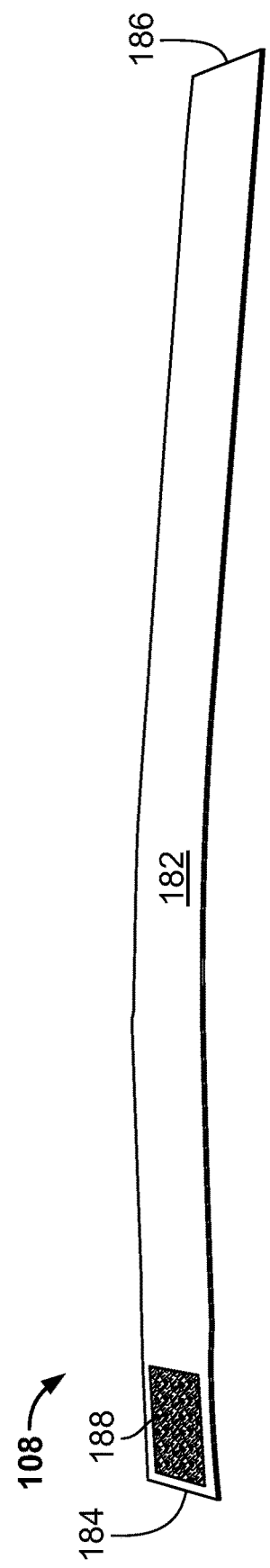
FIG. 18 shows a second side of the belt.

FIG. 17 shows a first side 180 of the belt 108. FIG. 18 shows a second side 182 of the belt. The belt 108 extends between a first end 184 and a second end 186. The belt 108 is made from a soft, breathable fabric material such that it can be comfortably worn by the patient P.

As shown in FIG. 18, the second side 182 of the belt 108 includes a fastener 188 at the first end 184. As shown in FIGS. 16-18, the fastener 188 can removably attach the first end 184 of the second side 182 to the first side 180 of the belt 108 to secure the belt 108 around the patient P's torso. The fastener 188 can be a hook-and-loop fastener, a hook-and-pile fastener, or a touch fastener. In some examples, the fastener 188 is a hook fastener. Additional types of fastening mechanisms for securing the belt 108 around a patient's torso may also be used.

Figure 19:
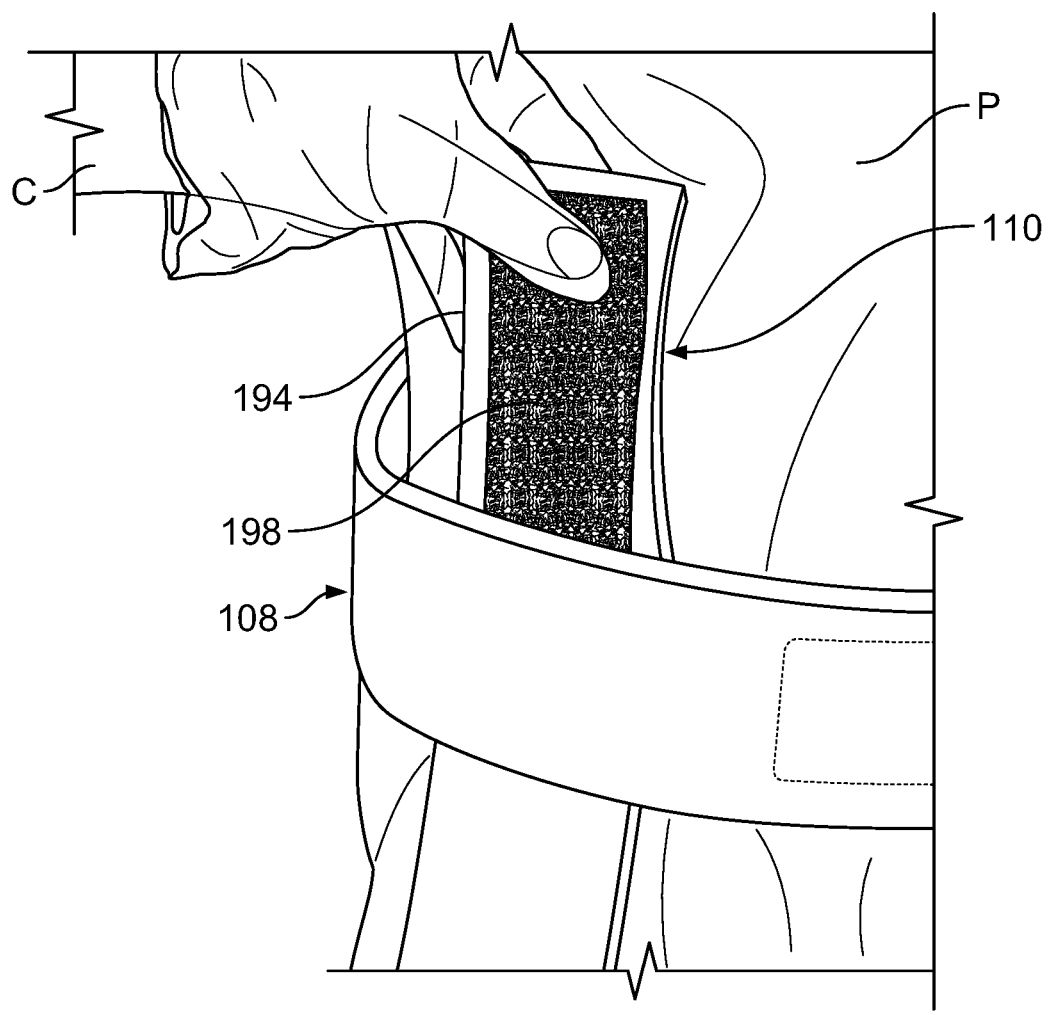
FIG. 19 shows an operation of the method of FIG. 15 being performed by a caregiver to slide a limb attachment strap of the kit of FIG. 1 under the belt.

Referring back to FIG. 15, the method 1500 next includes an operation 1504 of sliding a limb attachment strap 110 of the kit 10 (shown in FIG. 1) under the belt 108 that has been secured around the torso of the patient P. FIG. 19 shows operation 1504 being performed by a caregiver C to slide a limb attachment strap 110 under the belt 108.

Figure 20:
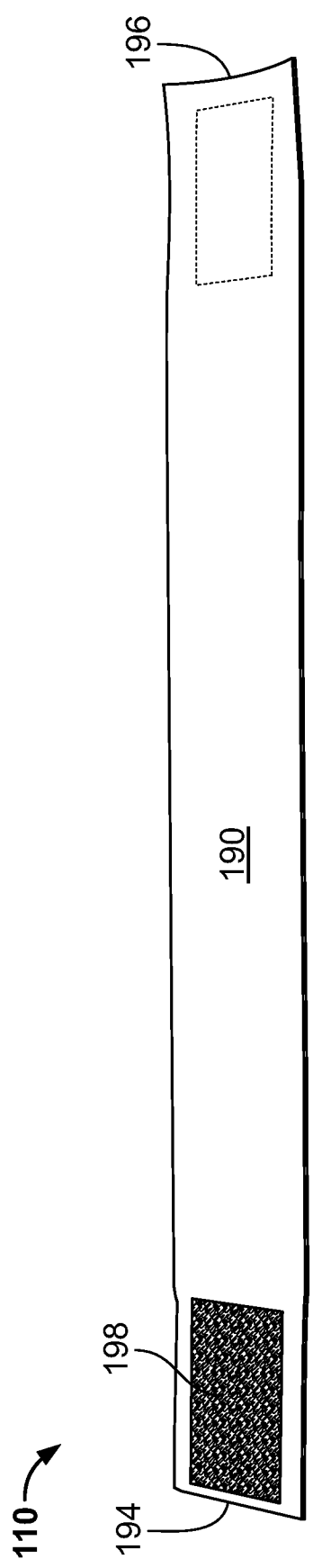
FIG. 20 shows a first side of the limb attachment strap.
Figure 21:
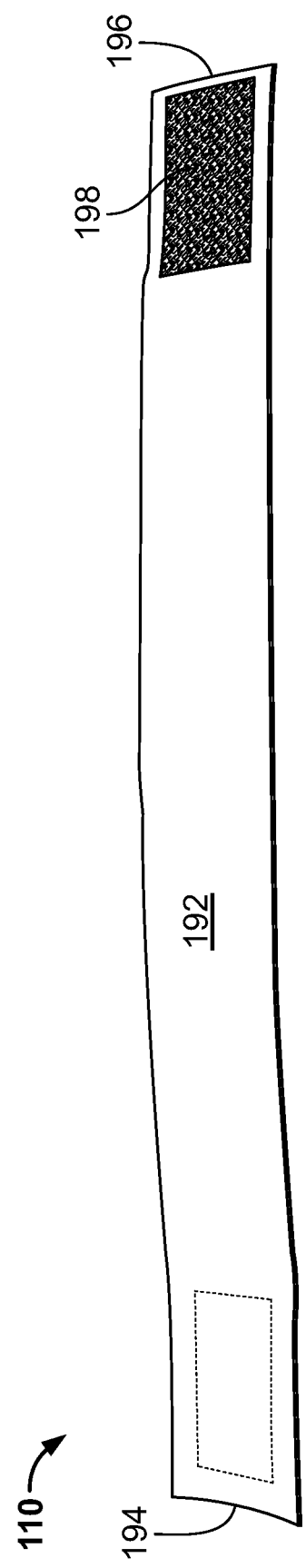
FIG. 21 shows a second side of the limb attachment strap.

FIG. 20 shows a first side 190 of the limb attachment strap 110. FIG. 21 shows a second side 192 of the limb attachment strap 110. The first and second sides 190, 192 of the limb attachment strap 110 face in opposite directions. The limb attachment strap 110 extends between a first end 194 and a second end 196. The limb attachment strap 110 can be made from the same material as the belt 108 such as a soft, breathable fabric material.

As shown in FIGS. 20 and 21, the first side 190 of the limb attachment strap 110 includes a fastener 198 toward the first end 194, and the second side 192 of the limb attachment strap 110 includes a fastener 198 toward the second end 196. The fastener 198 on the first side 190 faces an opposite direction of the fastener 198 on the second side 192.

The fasteners 198 on the first and second sides 190, 192 can be hook-and-loop fasteners, hook-and-pile fasteners, or touch fasteners. In some examples, the fasteners 198 are hook fasteners. Additional types of fastening mechanisms may also be used.

Referring back to FIG. 15, the method 1500 next includes an operation 1506 of securing the limb attachment strap 110 to the belt 108. As shown in FIGS. 19-21, the caregiver C can fold the first end 194 of the limb attachment strap 110 over the belt 108 such that the fastener 198 on the first side 190 can be used to loop and secure the first end 194 around the belt 108.

Figure 22:
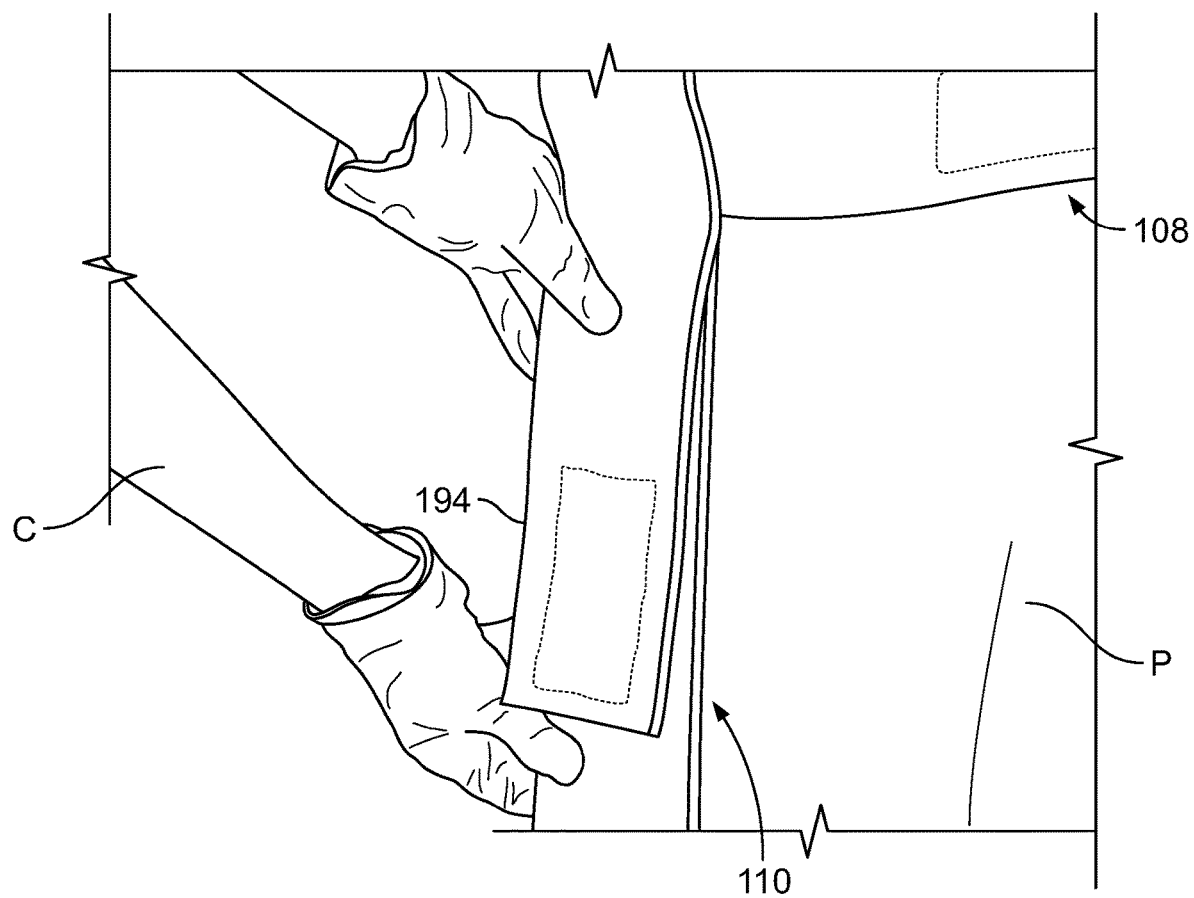
FIG. 22 shows an operation of the method of FIG. 15 being performed by a caregiver to secure the limb attachment strap to the belt.

FIG. 22 shows the first end 194 of the limb attachment strap 110 secured around the belt 108 (i.e., after completion of operation 1506). Advantageously, the fastener 198 on the first side 190 can removably attach to anywhere along the length of the limb attachment strap 110 to adjust the length that the limb attachment strap 110 extends from the belt 108.

Figure 23:
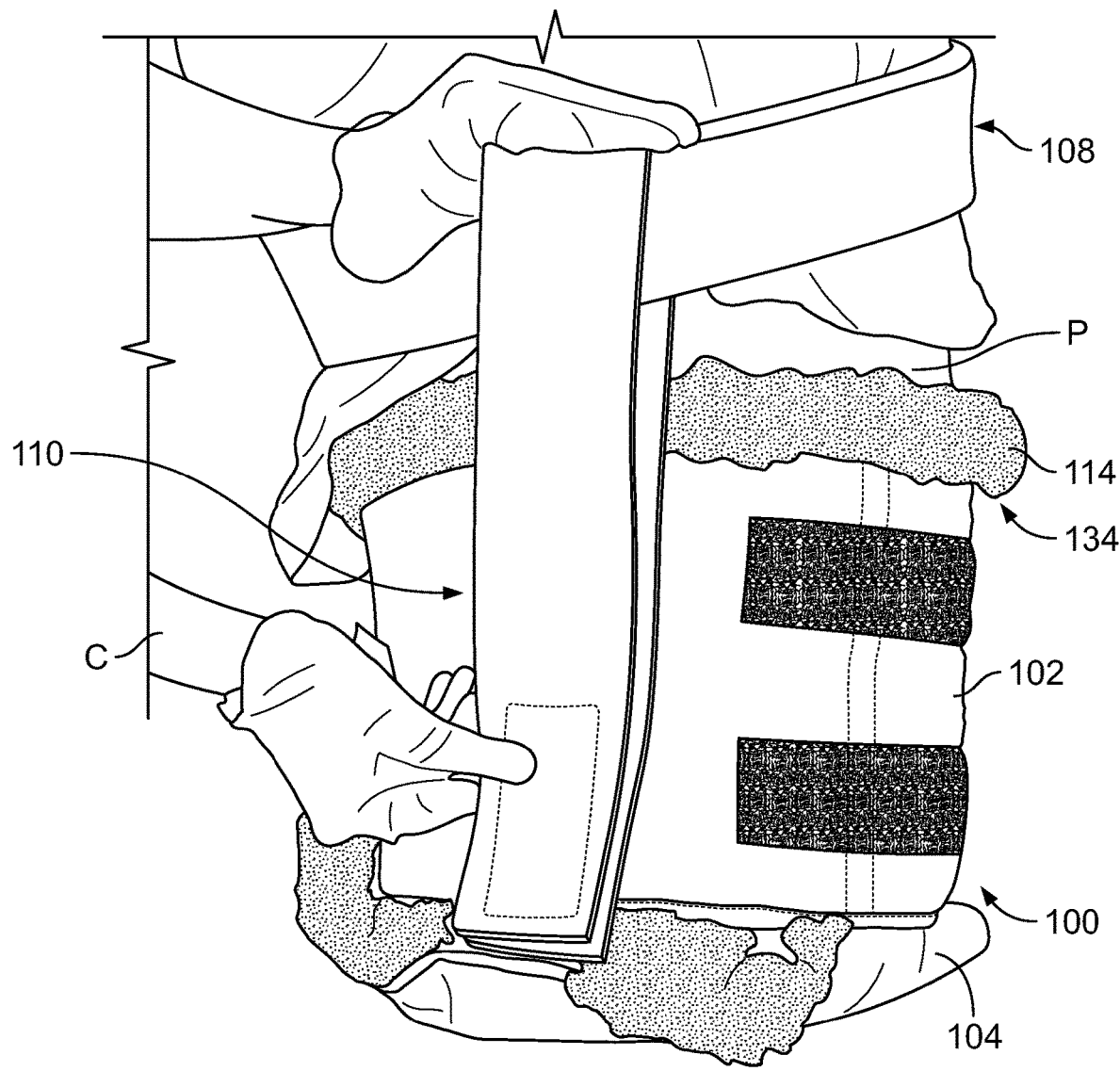
FIG. 23 shows an operation of the method of FIG. 15 being performed by a caregiver to secure the limb attachment strap to the leg protector.

Referring back to FIG. 15, the method 1500 next includes an operation 1508 of securing the limb attachment strap 110 to the leg protector 100. FIG. 23 shows a caregiver securing the second end 196 of the limb attachment strap 110 to the leg protector 100. As discussed above, the fastener 198 on the second side 192 of the limb attachment strap 110 faces in an opposite direction of the fastener 198 on the first side 190.

As shown in FIG. 23, the fastener 198 on the second side 192 of the limb attachment strap 110 can removably attach over the first flap 176 or the second flap 178 of the end piece 104 (when the first and second flaps 176, 178 of the end piece 104 are attached to the fasteners 144 on the exterior surface 120 of the thigh piece 102) to anchor the leg protector 100 covering the amputated leg to the belt 108 worn around the torso of the patient P.

Operations 1504-1508 can be repeated to anchor the leg protector 100 to the belt 108 with a second limb attachment strap. For example, a first limb attachment strap can be used to anchor a first side of the leg protector 100 (e.g., where the first flap 176 attaches to the thigh piece 102), and a second limb attachment strap can be used to anchor a second side of the leg protector 100 (e.g., where the second flap 178 attaches to the thigh piece 102).

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A kit for removably dressing a leg amputated above-knee, the kit comprising:
    a leg protector, the leg protector including:
        a thigh piece configured to wrap around a thigh of the leg; and
        an end piece configured to removably attach to the thigh piece, and to wrap around a distal end of the leg;
    a belt configured to be secured around a torso; and
    one or more limb attachment straps, each limb attachment strap configured to attach the belt to at least one of the thigh piece or the end piece to anchor the leg protector to the torso, each limb attachment strap extending between a first end and a second end, each limb attachment strap having a first hook-and-loop fastener positioned toward the first end, and a second hook-and-loop fastener positioned toward the second end, wherein each limb attachment strap includes a first side having the first hook-and-loop fastener, and a second side having the second hook-and-loop fastener, wherein the first hook-and-loop fastener on the first side faces an opposite direction of the second hook-and-loop fastener on the second side, and wherein the first hook-and-loop fastener removably attaches to anywhere along a length of the first side of the limb attachment strap for looping the first end of the limb attachment strap around the belt to secure the first end of the limb attachment strap to the belt, and the second hook- and loop fastener removably attaches the limb attachment strap to the leg protector wherein the thigh piece is configured to wrap around the thigh of the leg about a first axis of rotation, wherein the end piece is configured to wrap around the distal end of the leg about a second axis of rotation, and wherein the first and second axes of rotation are orthogonal with respect to one another.

2. The kit of claim 1, further comprising:
    a distal spacer for reducing a space between an interior surface of the end piece and the distal end of the leg.

3. The kit of claim 1, further comprising:
    scissors for cutting between lines of stitching on the thigh piece to adjust a length of the thigh piece while maintaining the integrity of the thigh piece.

4. The kit of claim 1, wherein a first limb attachment strap is configured to anchor a first side of the leg protector to the torso, and wherein a second limb attachment strap is configured to anchor a second side of the leg protector to the torso.

5. The kit of claim 1, wherein the thigh piece includes a first portion and a second portion, the first portion is configured to be placed at least partially under the thigh of the leg and the second portion is configured to be at least partially wrapped over the leg, and the first portion includes a cushion layer and a resilient layer positioned between interior and exterior surfaces.

6. The kit of claim 5, wherein the second portion includes lines of stitching that allow the second portion to be trimmed with scissors to adjust a length of the thigh piece.

* * * * *